(12) United States Patent
Murokh

(10) Patent No.: US 6,429,889 B1
(45) Date of Patent: Aug. 6, 2002

(54) LASER MARKING DISCRETE CONSUMABLE ARTICLES

(75) Inventor: Igor Y. Murokh, Santa Monica, CA (US)

(73) Assignee: Tri-Star Technologies, El Segundo, CA (US)

( * ) Notice: Subject to any disclaimer, the term of this patent is extended or adjusted under 35 U.S.C. 154(b) by 0 days.

(21) Appl. No.: 09/360,233

(22) Filed: Jul. 23, 1999

(51) Int. Cl.[7] .......................... B41J 2/435; B23K 26/00
(52) U.S. Cl. ..................... 347/224; 219/121.6
(58) Field of Search .................. 347/224, 262, 347/235, 234, 248; 524/360; 219/121.71, 121.85, 121.7, 121.6, 121.61

(56) References Cited

U.S. PATENT DOCUMENTS

| | | | |
|---|---|---|---|
| 3,657,510 A | 4/1972 | Rothrock | 219/121.11 |
| 4,595,647 A | 6/1986 | Spanjer | 430/138 |
| 4,753,863 A | 6/1988 | Spanjer | 430/138 |
| 4,769,310 A | 9/1988 | Gugger et al. | 430/346 |
| 4,906,813 A | 3/1990 | Gajdos | 219/121.68 |
| 5,030,551 A | 7/1991 | Herren et al. | 430/495.1 |
| 5,091,284 A | 2/1992 | Bradfield | 430/292 |
| 5,111,523 A | 5/1992 | Ferlier et al. | 385/100 |
| 5,206,280 A | 4/1993 | Williams | 524/409 |
| 5,294,770 A | 3/1994 | Riddle et al. | 219/121.7 |
| 5,376,771 A * | 12/1994 | Roy | 219/121.71 |
| 5,415,939 A | 5/1995 | Yeung | 428/422 |
| 5,489,639 A | 2/1996 | Faber et al. | 524/417 |
| 5,501,827 A | 3/1996 | Deeney et al. | 264/460 |
| 5,560,845 A | 10/1996 | Birmingham, Jr. et al. | 219/121.85 |
| 5,568,177 A | 10/1996 | Talvalkar et al. | 347/217 |
| 5,697,390 A | 12/1997 | Garrison et al. | 132/321 |
| 5,698,119 A * | 12/1997 | Geerke | 219/121.7 |
| 5,773,494 A | 6/1998 | Gusi | 524/14 |
| 5,789,466 A | 8/1998 | Birmingham, Jr. et al. | 523/213 |
| 5,798,037 A | 8/1998 | Peacock | 210/85 |
| 5,845,264 A | 12/1998 | Nellhaus | 705/28 |
| 5,916,943 A * | 6/1999 | Heller et al. | 524/360 |
| 6,108,026 A * | 8/2000 | Corbett | 347/262 |

FOREIGN PATENT DOCUMENTS

EP WO 91/01884 * 2/1991 ........... B41F/17/36

* cited by examiner

Primary Examiner—Hai Pham
(74) Attorney, Agent, or Firm—Bruce A. Jagger

(57) ABSTRACT

A unique method of marking individual consumable articles such as tablets, pills, and the like on the fly, without the deposition of ink or other marking materials on their surfaces, without degrading the articles, and without precise positioning and holding of the articles. Titanium dioxide is provided in a visible layer of the consumable articles in an amount that is effective to provide a mark when exposed to an effective amount of ultraviolet laser energy. The energy is emitted in a predefined pattern on the surface of the articles so as to define the desired marking pattern. Marking is effectively instantaneous, thereby permitting the target articles to be marked while in motion to efficiently and inexpensively provide marking rates that are as much as twenty times more than those provided by prior art ink deposition systems. Marking can be accomplished even when the articles are encapsulated in ultraviolet transparent packaging.

19 Claims, 2 Drawing Sheets

LASER MARKING DISCRETE CONSUMABLE ARTICLES

BACKGROUND OF THE INVENTION

1. Field of the Invention

The invention relates in general to directly marking discrete consumable articles such as pills, capsules, tablets, and the like; and, in particular, to rapidly marking such discrete articles on the fly without the deposition of any ink or other external marking material to the articles, and without degrading the articles. With the use of ultraviolet laser energy such articles can be precisionly marked at rates of speed previously unobtainable, and while the articles remain in continuous motion. Uniquely, the marking can be accomplished even when the articles are fully encapsulated in a transparent package.

2. Description of the Prior Art

The pharmaceutical industry today produces billions upon billions of human consumable articles such as therapeutically effective pills, tablets, jell-caplets, and the like. These articles contain a wide variety of different prescription and non-prescription drugs, and due to the wide variety and large production quantity of these consumed articles numerous health problems and concerns have arisen. For example, there has become an increasing need to provide direct identification on each individual consumable article, particularly therapeutically effective articles, so their contents can be traced at a later date. This has been found to be very valuable for the elderly where over prescription problems can result, as described in Nellhaus U.S. Pat. No. 5,845,264. Nellhaus describes the application of bar codes directly to consumable drugs by utilizing conventional high resolution printing techniques. These techniques deposit selected amounts of a marking material directly on the surface of the drugs, such as non-toxic or inert ink. A common technique is to apply food grade ink approved by the Food and Drug Administration with an ink jet or rotary wheel printer.

Individually marking individual consumable article has many advantages. For one, the articles can always be identified and distinguished from other articles even when removed from their containers or packaging. In addition, they can always be distinguished from other non-pharmaceutical consumable articles such as candies, and the like. With the individual marking of each consumable article, serious life threatening mistakes can be avoided. Such individual marking is also advantageous as accidental overdose situations, and the like, can be more quickly diagnosed.

Ablative laser marking of tablets had been proposed previously. Gajdos U.S. Pat. No. 4,906,813 teaches treating tablets with a gas laser beam to induce marking by ablatively burning off layers of the tablets. Riddle U.S. Pat. No. 5,294,770 teaches drilling drug release ports in pharmaceutical tablets with a laser. Undesirably, in both of these teachings, the laser energy is provided at such a high concentration as to physically burn off material from the surface of the tablet, that is, ablatively remove a portion of the material from the tablet. The removal leaves voids that can readily be seen with a 5X or less powered microscope. This ablation can cause many problems. Clear, sharp marking is difficult to achieve depending on the amount of chipping that occurs due to the ablative activity. In addition, the burning caused by the laser may chemically alter the remaining material of the tablet near the mark, which is highly undesirable in pharmaceutical applications. Thus, in order to make it feasible to mark consumable articles with a laser, a non-ablative method is needed.

Lasers are not presently used to mark consumable articles. Instead, the prior proposed expedients for marking pills utilized ink, frequently the ink jet process, wherein a precisely controlled amount of an edible or inert ink material was deposited directly on the surface of the pill in a predefined pattern. The prior equipment for marking pills was large, expensive, and required high maintenance. As such, the prior equipment was inherently less than perfect and introduced a significant cost increase in the production process.

Ink marking requires precise control of the objects in order to positively and accurately deposit the ink. This is troublesome since consumable articles are very small, and they must be mass produced. Individually marking each consumable article at a cost effective rate has proven to be problematic. Production rates are limited because each article must be securely held in position relative to an ink depositing instrument. The production rate may also be undesirably reduced since each freshly marked article must not be disturbed for a particular period of time dictated by the drying requirements of the ink.

Another problem with ink marking technology is maintaining the precise location of the ink head to the article in order to apply the desired amount of ink. This is further complicated when the articles are not of a uniform size in a given batch or from batch to batch of the same or different products. A change in size or shape requires a retooling of the marking equipment. When this precise positioning is not adequately controlled, too much or too little ink may be applied, undesirably resulting in an increased scrap rate. These problems exist with ink imprinting procedures such as ink jets, stamps, rollers and the like.

Still yet another problem is that ink feed devices such as ink jet heads are inherently subject to clogging. Clogging not only increases maintenance costs, but when ink feeds clog during a marking production run, a large quantity of tablets or pills may have to be scrapped. A high scrap rate is highly undesirable.

However, one of the greatest drawbacks to utilizing ink technology to mark consumable articles is the cost associated with preparing the articles for marking. Contaminants, such as organic oils and the like, on the surface of the articles must be removed prior to marking. These contaminants undesirably reduce or eliminate legibility and durability of the ink marking. Their removal requires that special pre-treatment cleaning systems be incorporated into the process. Most pharmaceutical articles require the application of a coating of oil on their surfaces during processing, and this coating must be removed prior to marking with conventional ink techniques. Thus, in pharmaceutical applications, a special pre-treatment cleaning system is required prior to marking. The equipment used to accomplish the pre-treatment cleaning is undesirably large and expensive, and also requires high maintenance.

Given the above problems, the prior art ink based marking systems could achieve maximum production marking rates of only about 1,200 pills per minute, or 72,000 per hour.

Another drawback in utilizing ink based processes to mark consumable articles is that the ink dispenser must be close to or in direct contact with the surface of the articles to be marked. Because the prior art printing techniques required that the printing mechanism have direct access to the surfaces that were to be marked, products that had already been encapsulated in packaging materials could not be marked. It would be highly desirable to be able to mark such articles after they are encapsulated in packaging. This permits greater flexibility in production operations.

Another limitation of the prior art equipment is that the edible or inert marking material must satisfy Federal food and drug regulations. Thus, it would be very desirable to mark these articles without introducing any additional material.

When ultraviolet energy is absorbed by certain titanium dioxide containing materials, the titanium dioxide changes color. This phenomena has been successfully utilized to provide markings on various non-consumable objects such as wire insulation, electronic components, ceramics, glass, plastics, and the like. See. for instance, U.S. Pat. Nos. 5,501,827, 5,091,284, 5,415,939, 5,697,390, 5,111,523, 4,595,647, 4,753,863, 4,769,310, 5,030,551, 5,206,280, 5,773,494, 5,489,639, and 5,798,037, describe laser marking of non-consumable articles made from various materials.

Those concerned with these problems recognize the need for an improved method of marking consumable articles.

These and other difficulties of the prior art have been overcome according to the present invention.

BRIEF SUMMARY OF THE INVENTION

One object of the present invention is to provide a method of marking discrete consumable articles without the deposition of ink or other marking material on the articles.

Another object of the present invention is to provide a high speed method of marking discrete consumable articles such that the articles can be marked on the fly, that is, they can be marked while they are in continuous motion.

Another object of the present invention is to provide a method of marking discrete consumable articles at higher resolutions than currently possible using ink deposition techniques such as ink jet printing, and the like.

Yet another object of the present invention is to provide a method of marking discrete consumable articles even though they have been encapsulated in their final transparent packaging.

It is yet another object of the present invention to provide a method of marking discrete consumable articles that does not require a pre-treatment cleaning process or post-treatment curing process.

Still yet another object of the present invention is to mark discrete consumable articles without etching or physically degrading the articles.

As used herein, "consumable articles" are articles intended to be consumed, orally or otherwise, by a living being, human or non-human, for therapeutic purposes, including prescription, non-prescription and food supplements. Examples of such discrete consumable articles include pills, tablets, gel caplets, dissolving tablets, lozenges, and the like.

According to the present invention individual consumable articles are marked by the application of irradiation energy, and without the deposition of any ink or other external marking material, and without physically degrading the articles. As used herein, a "non-deposited marking" is a marking in which no marking material, such as ink, paint or the like, is physically applied to an article during the marking process. Physical degradation results when the amount or nature of the energy applied to an article causes that article to burn, melt, vaporize, or otherwise degrade leaving a crater or an otherwise visibly damaged area that is readily visible with an optical microscope having a magnification factor of 5× or less. Such physical degradation can also include chemical degradation that alters the therapeutic nature of the product. Therapeutic degradation is not necessarily visible, however, such degradation of therapeutic effectiveness can be detected by chemical or biological analysis. Chemical degradation occurs when the degradation is sufficient to materially impair the therapeutic effectiveness of the dosage that is in one article. Trace degradation that has no material therapeutic effect is not considered to be physical degradation.

The method of the present invention comprises selecting a radiation sensitive first material that changes to a detectable color when exposed to laser energy, and incorporating an effective amount of that radiation sensitive material into a visible layer of the discrete consumable articles that are to be marked. Generally, but not necessarily, the radiation sensitive material is in the outer layer of the article. The discrete consumable articles are then preferably placed in motion and, preferably, a sensing location is established at a predetermined location or marking zone relative to a source of ultraviolet laser energy. The sensing location detects the arrival of a discrete article in the marking zone and triggers the firing of a laser. Alternatively, the laser can be moved relative to the articles and fired when it is in the proper position to mark an article, or both can be in motion when the laser is fired. The laser beam can be moved, without moving the laser, by the use of a suitable laser beam delivery system, if desired. Also, the firing of the laser can be synchronized to the relative movement of the articles to the laser by some means other than a sensor that detects the arrival of an article in the marking zone. For example, the mechanism can be synchronized so that the laser fires every time a particular station is passed by an article feed mechanism whether there is an article in position to be marked or not, or the like. Each of the articles is individually and instantaneously exposed to a predefined pattern of laser energy, preferably while it remains in motion. For purposes of economy a mask is very efficient in defining the pattern. Other pattern definition means can be used if desired. The laser energy is absorbed by the radiation sensitive first material in each consumable article according to the predefined pattern, and the first material, for example, changes color to provide the required detectable marking. In general, the detectable marking is visible to the unaided human eye. The marking may, however, be such as to be detectable by alternative means such as exposure to ultraviolet light, examination by a microscope, machine readers such as bar code readers, and the like, if desired.

Because the laser marking occurs substantially instantaneously, the articles can be marked while in motion at relatively high rates of speed. For example, the articles can be placed in motion by a conveyor system as is commonly used in many mass production facilities. However, the laser marking occurs so fast that it is possible to mark the articles as they fall vertically under the force of gravity, thus allowing marking to be accomplished as the articles fall from a vertical hopper, or the like. Other means of projection, such as, for example, centrifugal force, air pressure, or the like can also be used to place the articles in motion. The rate of the article's movement should be synchronized with the cycle time or pulse rate of the pulsed laser. If very rapid pulse rates are available it may be desirable to feed the articles at a rate that is faster than a mere gravity feed can achieve.

Significantly, no external marking material is applied to the articles at any time. Clogging problems and drying time requirements inherent in the prior art ink marking systems are completely eliminated. Pre-treatment cleaning systems and post-treatment curing processes are no longer necessary. The problems associated with precisely positioning the article relative to the ink applicators of the prior art are also eliminated.

Precise positioning of the article relative to the source of laser energy, according to the present marking process, is not required. All that is required is that the area of a consumable article that is to be marked be positioned within a relatively large focal range and roughly normal to a source of laser energy. Exposure to the source of laser energy is controlled so that no physical degradation occurs. With the essentially instantaneous marking of the articles, marking production rates are significantly increased, compared to prior art ink deposition marking systems.

According to one embodiment, 24,000 pills can be marked per minute, equating to 1,440,000 pills per hour. This is a substantial marking rate increase compared to prior art ink jet or inked rotary wheel techniques. For instance, it is twenty times faster than the conventional prior art production rate of about 1,200 pills per minute.

Because the marking results from the response to the laser energy of the radiation sensitive first material present in the articles, articles can be marked even when fully encapsulated in ultraviolet transparent packaging materials, such as clear plastics. For instance, many capsules are individually packaged on perforated tearable panels having a transparent encapsulation. It has been found that laser marking of these encapsulated capsules can be easily and effectively accomplished directly through these transparent encapsulations or wrappings. Likewise, the layer in which the marking develops need not be the outer layer of the article so long as the layer(s) on top of the marked layer are transparent to the radiation and the marking detecting means. The marking actually occurs in situ at and below the surface of the pigment containing layer. For the marking to be visible the layer, and those above it, must be transparent enough to the visible spectrum of light that the marking is visible. The layer need not be transparent. Because the marking is near the surface a colored layer that is opaque when its entire thickness is considered can still be sufficiently translucent for the marking to be clearly visible. Consumable articles are often white in appearance because of the presence of the pigment, titanium dioxide. Where there is sufficient pigment to color the object white, the absorption of the ultraviolet energy and the resultant marking, takes place very close to the surface so that the markings are clear.

According to a preferred embodiment, an effective amount of finely divided titanium dioxide is provided in the layer of the article that is to be marked. In this instance, the surface layer contains the titanium dioxide. When exposed to a predefined pattern of laser energy in the ultraviolet range of from about 380 to 190 nanometers, precisely marked articles are produced with virtually no scrap. The markings are generally black. The markings are embedded in the layer so they are not entirely on the surface where they might be subject to erasure. They are generally visible by reason of a light colored background. Titanium dioxide is conventionally present in numerous pharmaceutical tablets and jellcaps formulations, and the like. These products can be marked with a laser according to the present invention without changing the formulation of the product so that regulatory requalification is not required. The titanium dioxide in these formulations was often intended to function as a whitening agent for the articles, and not at all for the purpose of enabling laser marking of the articles.

Generally, it is preferred the titanium dioxide be comprised of the rutile crystalline form. Also, it is preferred that the titanium dioxide be substantially white.

The titanium dioxide particles should have average diameters of less than about 10 and preferably less than 5 microns. Particle sizes of less than approximately 2 microns average are preferred. Larger particles require the use of undesirably high energy pulses. Higher and longer pulses of energy risk physical degradation and can, in extreme situations, slow the process down. The maximum duration of the pulse increases approximately with the square of the particle diameter. The following formula can be used to approximately estimate the maximum duration of the pulse that can be tolerated before physical degradation occurs.

$$T = D^2 \rho C_p / \lambda$$

where T=pulse duration in nanoseconds, D=particle diameter in meters, $C_p$=the heat capacity of titanium dioxide (690.37 Joules per kilogram degree Kelvin), $\lambda$=the thermal conductivity of titanium dioxide (6.55 Watts per meter degree Kelvin), and $\rho$=the particle density (4,000 kilograms per cubic meter). Read literally, this equation produces an answer in seconds. For ease of use this is converted to nanoseconds. Pulses of longer duration than those indicated by this equation will result in the application of more energy than the titanium dioxide can absorb by itself. Pulses of shorter duration should be used to avoid damaging the target article. For a particle with an average diameter of about 0.5 microns the maximum pulse duration is approximately 100 nanoseconds. As will be understood by those skilled in the art, several approximations are made in the above equation which preclude relying on it to determine anything other than approximate order of magnitude of the maximum pulse duration times. For example, round particles are assumed. This is, of course, a very rough approximation for most particles. A constant particle diameter across all particles in the target is assumed. Again, this is only an approximation. There will always be some particle size distribution and agglomeration. This formula is useful in arriving at the order of magnitude of the maximum allowable pulse duration from which those skilled in the art can easily optimize a particular system. Effective marking can generally be achieved using significantly shorter pulses. For example, pulses of approximately 10 nanoseconds, an order of magnitude less than the maximum allowable duration, are generally effective in producing legible markings. The preferred optical pulse duration is from about 5 to 20 nanoseconds, but pulse durations of from approximately 5 to 200 nanoseconds are effective and can be employed, if desired. Some adjustment based on actual experimental results will generally be required to optimize the system. In general, the shortest pulse that is effective to produce a marking of the desired legibility should be used so as to minimize the risk of physically degrading the article. As the particle diameter increases more energy is required and the risk that energy will be dissipated by conventional heat and mass transfer processes beyond the pigment particles to the detriment of the article also increases substantially. For this reason the average diameter of the particles should be minimized.

The applied laser fluence or energy density (in Joules per square centimeter) is proportional to the diameter of the titanium dioxide particle. Without wishing to be bound by any particular theory it is believed that it should be assumed that the absorbed pulse of energy should be sufficient to heat the average pigment particle in the target article to its melting point. There should not be enough energy to change anything else in the target. Thus, where the pigment particles are the only part of the outer layers of the article that absorb ultraviolet energy, all of the energy should be absorbed by those particles. The following formula provides an approximation of the laser fluence (energy flow density) that is required.

$$F=2\rho C_p D(T_m-T_a)/3$$

Where F=the laser fluence (energy flow density) in Joules per square meter; $\rho$=the particle density (4,000 kilograms per cubic meter); $C_p$=the heat capacity of titanium dioxide (690.37 Joules per kilogram degree Kelvin); D=the diameter of the particle in meters; $T_m$=2116 degrees Kelvin, the melting point of titanium dioxide; $T_a$=the ambient temperature in degrees Kelvin. For ease of use the energy density is generally converted to Joules per square centimeter, and the particle diameter to microns. This equation establishes an energy threshold for a system where the pulse duration has already been established. This equation generally provides an approximation that tends to be in the middle to lower end of the acceptable range of energy flux. It provides an approximate bench-mark from which those skilled in the art can easily optimize a particular system. In general an energy flux density of from approximately 10 to 0.1, preferably, 5 to 0.1 Joules per square centimeter is effective to form a satisfactory marking. Generally an energy flux density of from approximately 1 to 0.1 is most preferred. The minimum amount of energy that is effective to produce the desired marking should generally be used. For a particle with a diameter of about 0.5 microns the starting approximation for the laser fluence is in the order of 0.17 Joules per square centimeter.

The above equations yield the following calculated values for the particle diameters that are indicated in Table I below.

TABLE I

| Particle Diameter - D (microns) | Energy Density - F (Joules/cm²) | Maximum Pulse Duration - T (nanoseconds) |
| --- | --- | --- |
| 0.10 | 0.03 | 4 |
| 0.25 | 0.09 | 25 |
| 0.35 | 0.12 | 49 |
| 0.50 | 0.17 | 100 |
| 0.75 | 0.26 | 225 |
| 1.0 | 0.34 | 400 |

The values given in Table I are order of magnitude values that provide those skilled in the art with a reliable starting point from which to optimize a particular system. Many different variables, not all of which are fully understood, enter into determining the optimum values for a particular system. For example, particle size distribution, the degree of pigment agglomeration that a particular processing system produces, and the like, all influence these values.

Energy density can generally be adjusted through a wide range to a predetermined level as may be desired. The pulse duration, by contrast, is generally a fixed characteristic of the laser. When a laser is selected for the purposes of this invention, this inherent characteristic should be kept in mind. Most generally available ultraviolet lasers have pulse durations of less than 100 nanoseconds.

The titanium dioxide should be present in the layer that is to be marked in an amount ranging from approximately 0.5 to 5 weight percent, based on the weight of the layer. Preferably, the titanium dioxide is present in an amount of from about 1 to 3 weight percent. The optimum density of the ultraviolet radiation on the article generally depends in part on the concentration of the titanium dioxide. Increasing the concentration of the titanium dioxide increases the risk of physical degradation. Below about 0.5 weight percent of titanium dioxide, the markings tend to become faint. As the concentration of the pigment increases the clarity of the marking improves up to a point where the particles are so close together that there is a risk of degradation by reason of the concentration of absorbed energy. Where the concentration is low, on average the energy is absorbed, and the marking occurs, deeper in the layer. The contrast is not as great where the concentration is so low that the marking occurs at a substantial depth in the layer. The concentration of pigment should be minimized as much as possible to avoid the necessity of using high energy densities consistent with achieving markings of acceptable contrast and crispness. Where the quality of the marking is not what is desired even at the maximum safe energy levels, the solution is to increase the concentration o f the pigment rather than to degrade the article by increasing the energy level. Above a certain pigment concentration, however, the amount of energy required to generate an acceptable marking increases to an unacceptable level where degradation of the article is likely to occur. In general, pigment concentrations of less than approximately 5 weight percent are acceptable. It is assumed that the pigment is all of approximately of the same size and is equally distributed in the layer that absorbs the energy. Some processing procedures do not provide such optimum uniform distribution. Such systems should be optimized for the particular size and bulk distribution according to the teachings of the present invention.

The optimal wavelength for the ultraviolet energy is that at which the titanium dioxide absorbs energy most strongly. This is below about 400 nanometers. In general, lasers that emit ultraviolet light in the range of from about 380 to 190 nanometers are useful with those that emit energy at about 360 to 240 nanometers being preferred.

Preferably, for high volume production requirements the laser should have a pulse rate of from at least about 10 to about 1000, preferably, 20 to 400 Hertz. Pulse rate is to be distinguished from pulse duration. These are different characteristics of any given laser. Pulse rate generally defines the maximum production rate. Pulse rate indicates how many times the ultraviolet laser fires in one second, which is usually described in number of events per second (Hertz). Pulse duration indicates how long the laser is illuminated during each pulse, and is described in nanoseconds.

Other objects, advantages, and novel features of the present invention will become apparent from the following detailed description of the invention when considered in conjunction with the accompanying drawings.

BRIEF DESCRIPTION OF THE DRAWINGS

The present invention provides its benefits across a broad spectrum of marking articles such as, for example, pills, tablets, capsules, and the like. While the description which follows hereinafter is meant to be representative of a number of such applications, it is not exhaustive. As those skilled in the art will recognize, the basic methods taught herein can be readily adapted to many uses. It is applicant's intent that this specification and the claims appended hereto be accorded a breadth in keeping with the scope and spirit of the invention being disclosed despite what might appear to be limiting language imposed by the requirements of referring to the specific examples disclosed.

Referring particularly to the drawings for the purposes of illustration only and not limitation.

DETAILED DESCRIPTION OF THE PREFERRED EMBODIMENTS

Figure 1:
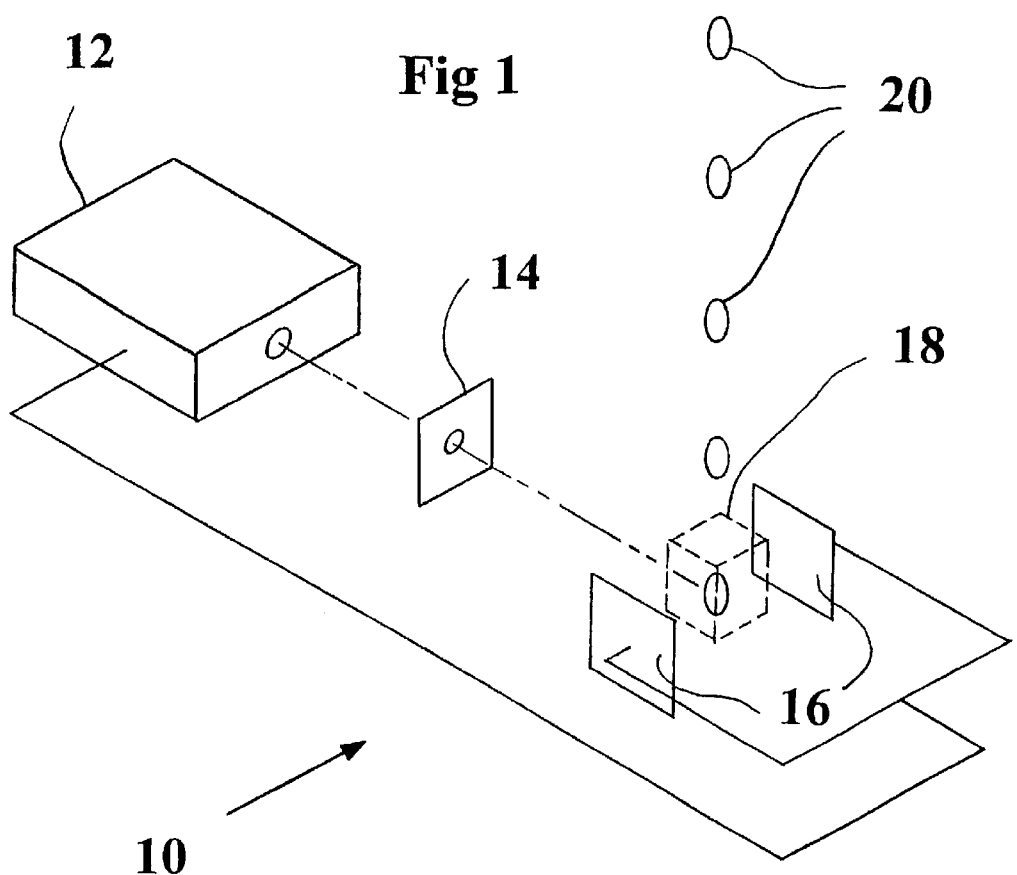
FIG. 1 is a schematic view of a preferred embodiment consumable article laser marking system of the present invention.
Figure 2:
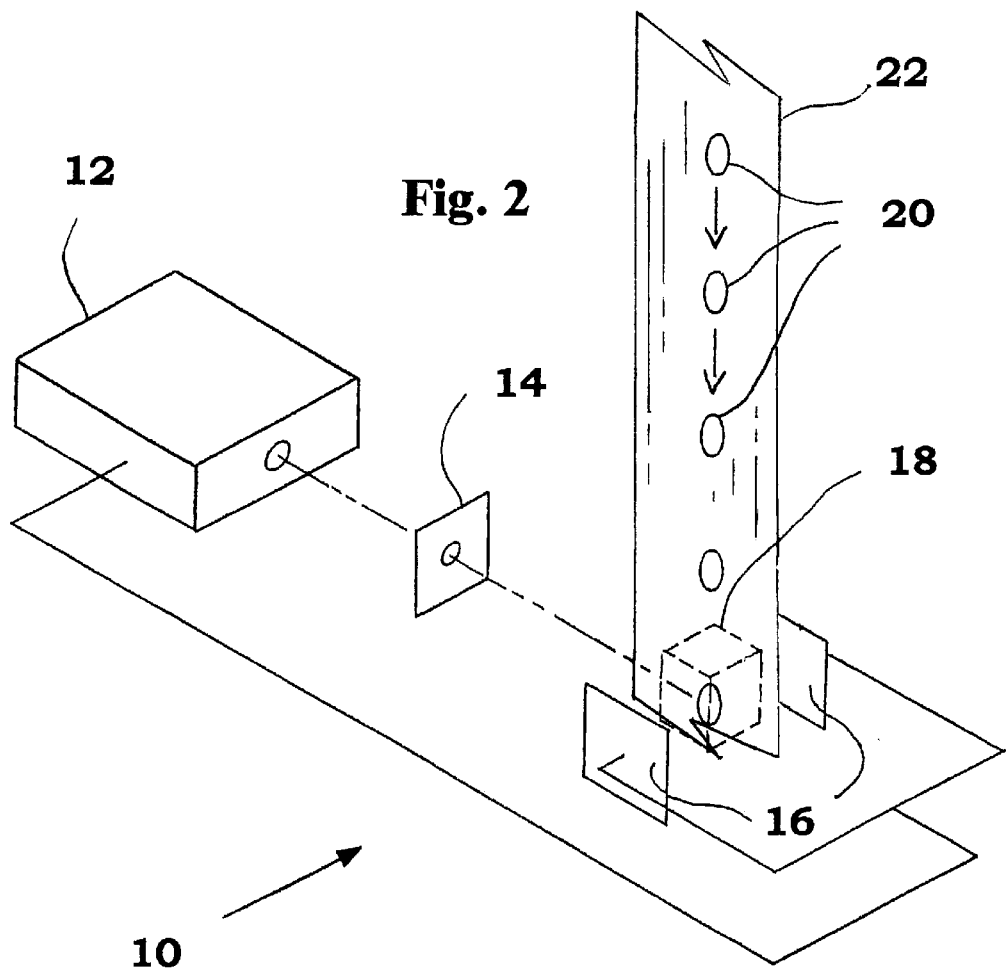
FIG. 2 is a schematic view similar to FIG. 1 illustrating the use of a conveyor for the consumable articles.

Referring particularly to the drawings there is schematically illustrated generally at 10 a consumable article laser marking system. The marking system comprises ultraviolet laser 12, a mask 14 in the configuration to allow the passage of a predefined pattern of ultraviolet energy, and sensor 16. The sensor 16 establishes a sensing location generally shown at 18. Consumable articles (pills) 20 are placed in continuous motion to travel through the sensing location 18. The sensor detects the presence of a consumable article as it passes through the sensing location 18 and, nearly instantaneously, sends a signal to the laser that an object is in the marking zone. The laser then emits a burst of coherent ultraviolet energy. The beam of energy passes through mask 14 and exposes article 20 to pattern of laser energy that is defined by mask 14. Pulsing the laser at 20 Hertz (Hz) permits the marking of up to 20 pills per second. Pulsing the laser at 200 Hertz permits the marking of up to about 200 pills per second. Alternatively, conveyor 22 carries the articles 20 through the sensing location 18.

Numerous lasers are available that can be operated in the ultraviolet region. Where high production rates in excess of 200 articles per second or more are required, ultraviolet excimer lasers, for example, can be used. Various fixed and moving masks can be used, as desired. Due to the very short pulse duration, consumable articles can be marked on the fly, that is, while continuously moving at high rates of speed through the marking zone. The length of the pulse compared to the velocity of the article is such that the article is essentially frozen in place during the pulse. The instantaneous position of the article does not change enough during the marking step to cause any perceptible blurring of the marking. Various article feed mechanisms can be used. Where high rates of production are required, gravity feed may not be fast enough. The articles to be marked must be accelerated to speeds that will accommodate high production rates. Marking at even very high rates of production, for example, 400 articles per second, can be achieved at high resolution and with little or no scrap rate.

Marking is achieved when titanium dioxide absorbs energy that is emitted in the ultraviolet region, undergoes a photochemical change, and turns from white to black. Most significantly, titanium dioxide is also generally regarded as safe for human consumption. The amount of energy in the ultraviolet wavelengths, which is effective to cause the titanium dioxide to change color, is substantially completely absorbed by the titanium dioxide. Energy in other parts of the spectrum, for example, the infrared, would cause heating to a much greater depth and over a much wider area with the potential for damaging the pill through physical degradation. Preferably, the ingredients in the marking layer, other than the titanium dioxide, are substantially transparent to the radiation. Also, to the extent possible the rest of the article should be transparent to the radiation, although it can be, for example, reflective of the ultraviolet radiation.

In the preferred embodiment that has been selected for purposes of illustration only and not limitation, consumable articles having an effective amount of titanium dioxide in their outer surface layer, about 2 percent by weight of the outer layer, provide satisfactory marking results when exposed to ultraviolet laser energy at a wavelength of 355 nanometers, a pulse rate of 20 Hertz, a pulse duration of 10 nanoseconds, and a pulse energy of 20 milliJoules optically condensed to give a density of about 1 Joule per square centimeter of the marked area. In general, the amount of titanium dioxide is preferably limited to that which is effective to produce the desired visible marking. Excess amounts serve no useful purpose, and can be detrimental. Preferably, the titanium dioxide need only be present in an effective amount in the layer of the articles where marking is to occur, but may be present throughout the entire volume of the article, if desired. The thickness of the layer that contains the effective amount of titanium dioxide need only be a few mills thick, if desired.

It is unclear why ultraviolet laser energy, when applied to articles containing titanium dioxide, produces clear and sharp markings. Although applicant does not intend to be limited to any theory, it is believed that the ultraviolet laser energy, when delivered to the titanium dioxide at a wavelength that it can absorb, and for a very short time duration yet at a high power level, causes some structural modification to the titanium dioxide molecules, and this structural modification is visibly detectable as a change in color. It is not believed that the laser energy burns the material that surrounds the titanium dioxide since the time duration of exposure is so small, and also because no holes or voids are present on the surface of the articles when viewed with an optical microscope at a magnification factor of 5×.

In one embodiment, a Nd:YAG pulse laser is used. In this embodiment, in which the laser operated at 20Hz, consumable articles are capable of being marked at a rate of about 1,200 per minute (720,000 per hour). This marking rate is competitive with conventional ink deposition marking systems.

It is to be appreciated that other lasers can be used, as desired, for purposes of increasing the marking rate. For example, an Xe:Cl excimer laser may be used, as desired, operating at up to as much as 400 Hz. Utilizing such a laser at 400 Hz provides the potential to mark the consumable articles at 24,000 per minute, (1,440,000 per hour) which is many times faster than the conventional prior art ink deposition marking systems. For example, the LPX 100i series Xe:Cl excimer laser, produced by Lambda Physik Inc., operating at 400Hz and producing 100 miliJoules of laser energy at a wavelength of 308 nanometers, could easily achieve the substantially increased marking rates discussed above. Other lasers may be used, as desired, such as solid state lasers (i.e. Nd:YAG, or Nd:YFL), or gaseous excimer lasers (XeCl, KrF, ArF, or F2), as long as the wavelength, energy density, and pulse duration, are effective to produce the desired marking.

The rate at which the target articles are moving in the marking zone is so slow, even at a rate of 400 articles per second, compared to the duration of the laser pulse, that the target articles are assumed to be stationary at the time of marking. Thus, the articles can be moving at a constant rate, or they can be accelerating or decelerating without having any significant impact on the quality of the marking. The efficiency of the system depends in significant part on the fact that the target articles can be marked while they are in motion, and without elaborate positioning procedures and equipment. Preferably, the marking area of the target article is substantially perpendicular to the beam of energy, although misalignment of as much as, for example, 10 degrees, more or less, can be tolerated without rendering the marking unintelligible due to distortion. Even at greater angles the marking will still occur, but it may be so distorted that it is not easy to read. Since there is no physical impact required to accomplish the desired marking, the target article need not be supported in any way. That is, it is free standing. Thus, it is feasible to mark an article while it is in free flight under the influence of gravity or after it has been discharged from a projecting device.

What have been described are preferred embodiments in which modifications and changes may be made without departing from the spirit and scope of the accompanying claims. Many modifications and variations of the present invention are possible in light of the above teachings. It is therefore to be understood that, within the scope of the appended claims, the invention may be practiced otherwise than as specifically described.

What is claimed is:

1. A method of applying detectable non-deposited identification markings on discrete consumable articles, said discrete consumable articles being intended for consumption by a living being for therapeutic purposes, comprising the steps of:
   selecting a radiation sensitive material that is adapted to provide a said detectable non-deposited identification marking when exposed to ultraviolet laser energy;
   including an effective amount of said material in at least a visible part of said consumable articles;
   providing a source of pulsed ultraviolet laser energy;
   moving said consumable articles relative to said source of pulsed ultraviolet laser energy until one of said consumable articles is positioned within a marking zone;
   synchronizing the pulse of said ultraviolet laser energy with the positioning of said one consumable article in said marking zone;
   exposing said one consumable article in said marking zone to a pulse of ultraviolet laser energy in a predefined pattern, said pulse of ultraviolet laser energy being effective to cause said material in said one consumable article to change to said detectable non-deposited identification marking where exposed to said pulse of ultraviolet laser energy, and said pulse of ultraviolet laser energy being insufficient to cause visible physical degradation of said one consumable article.

2. A method of applying detectable non-deposited identification markings on consumable articles according to claim 1 including exposing said one consumable article to said pulse of ultraviolet laser energy while said one consumable article is in continuous motion.

3. A method of applying detectable non-deposited identification markings on consumable articles according to claim 2 including exposing at least about 20 of said one consumable articles per second to said pulse of ultraviolet laser energy.

4. A method of applying detectable non-deposited identification markings on consumable articles according to claim 2 including exposing at least about 200 of said one consumable articles per second to said pulse of ultraviolet laser energy.

5. A method of applying detectable non-deposited identification markings on consumable articles according to claim 1 including selecting titanium dioxide as said radiation sensitive material.

6. A method of applying detectable non-deposited identification markings on consumable articles according to claim 1 including moving said consumable articles by gravitational forces.

7. A method of applying detectable non-deposited identification markings on consumable articles according to claim 1 including moving said consumable articles by a conveyor.

8. A method of applying detectable non-deposited identification markings on consumable articles according to claim 1 wherein said pulse of ultraviolet laser energy is sufficient to at least partially melt said material.

9. A method of applying detectable non-deposited identification markings on consumable articles according to claim 1 including selecting a particulate form of said radiation sensitive material, said radiation sensitive material having an average particle size of less than about 10 microns.

10. A method of applying detectable non-deposited identification markings on consumable articles according to claim 1 including selecting a particulate form of said radiation sensitive material, said radiation sensitive material having an average particle size of less than about 1 micron.

11. A method of applying detectable non-deposited identification markings on consumable articles according to claim 1 wherein said pulse of ultraviolet laser energy has a pulse duration of less than about 200 nanoseconds.

12. A method of applying detectable non-deposited identification markings on consumable articles according to claim 1 including exposing said one consumable article to said pulse of ultraviolet laser energy while said one consumable article is in motion in said marking zone.

13. A method of applying detectable non-deposited identification markings on consumable articles according to claim 1 including exposing said one consumable article while it is in free flight.

14. A method of applying detectable non-deposited identification markings on discrete consumable articles, said discrete consumable articles being intended for consumption by a living being for therapeutic purposes, said method comprising the steps of:
   including an effective amount of titanium dioxide having a first color in a visible layer in each of said consumable articles;
   placing said consumable articles in motion;
   exposing each of said consumable articles to a patterned pulse of ultraviolet laser energy while said consumable articles are in motion, the duration and density of said pulse of ultraviolet energy being effective to cause said first color to change to a second color where exposed to said laser energy, said exposing being insufficient to cause said consumable articles to exhibit physical degradation where exposed to said pattern of ultraviolet light when viewed at no more than about 5 power magnification.

15. A method of non-degradively marking a discrete consumable article for identification purposes with a laser emitting ultraviolet energy, said consumable article being intended for consumption by a living being for therapeutic purposes, said method comprising the steps of:
   including from about 0.5 to 5 weight percent of particulate titanium dioxide in an outer layer of said consumable article, said particulate titanium dioxide having an average particle size of less than about 10 microns;
   exposing said outer layer of said consumable article to a predefined pattern of ultraviolet laser energy for no longer than approximately 200 nanoseconds at a density of less than about 10 Joules per square centimeter, said energy having a wavelength of between about 190 to 380 nanometers.

16. A method of non-degradively marking a discrete consumable article for identification purposes according to claim 15 including exposing said outer layer at a density of from approximately 1 to 0.1 Joules per square centimeter.

17. A discrete consumable article, said consumable article being intended for consumption by a living being for therapeutic purposes, said discrete consumable article comprising from about 0.5 to 5 weight percent of titanium dioxide, said titanium dioxide having an average particle size of less than about 10 microns, said titanium dioxide being in a visible layer thereof, except for said titanium dioxide said visible layer being substantially transparent to ultraviolet radiation, said titanium dioxide having a first color, a portion of said titanium dioxide in a predefined pattern having a different color from said first color, said different color being formed in situ in said visible layer in a region on said discrete consumable article, said consumable article exhibiting no physical degradation in said region when viewed at no more than about 5 power magnification.

18. A method of applying detectable non-deposited identification markings on discrete consumable articles, said discrete consumable articles being intended for consumption by a living being for therapeutic purposes, comprising the steps of:

selecting a radiation sensitive first material that is adapted to provide a said detectable non-deposited identification marking when exposed to ultraviolet laser energy;

including an effective amount of said first material in at least a visible part of said consumable articles;

packaging said consumable articles in a package comprising a second material, said second material being substantially ultraviolet transparent;

providing a source of pulsed ultraviolet laser energy;

positioning said consumable articles so that said second material is interposed between said source and said consumable articles, and moving said consumable articles relative to said source of pulsed ultraviolet laser energy until one of said consumable articles is positioned within a marking zone;

synchronizing the pulse of said ultraviolet laser energy with the positioning of said one consumable article in said marking zone;

exposing said one consumable article in said marking zone through said second material to a pulse of ultraviolet laser energy in a predefined pattern, said pulse of ultraviolet laser energy being effective to cause said first material in said one consumable article to change to said detectable non-deposited identification marking where exposed to said pulse of ultraviolet laser energy, and said pulse of ultraviolet laser energy being insufficient to cause visible physical degradation of said one consumable article when viewed at no more than about 5 power magnification.

19. A method of applying detectable non-deposited identification markings on discrete consumable articles, said discrete consumable articles being intended for consumption by a living being for therapeutic purposes, said method comprising the steps of:

including an effective amount of titanium dioxide having a first color in a visible layer in each of said consumable articles;

providing packaging material for said consumable articles;

exposing each of said consumable articles to a patterned pulse of ultraviolet laser energy through said packaging material, the duration and density of said pulse of ultraviolet energy being effective to cause said first color to change to a second color where exposed to said laser energy without causing visible physical degradation of said consumable articles when viewed at no more than about 5 power magnification.

* * * * *

(12) EX PARTE REEXAMINATION CERTIFICATE (10831st)
United States Patent
Murokh

(10) Number: US 6,429,889 C1
(45) Certificate Issued: Mar. 15, 2016

(54) LASER MARKING DISCRETE CONSUMABLE ARTICLES

(75) Inventor: Igor Y. Murokh, Santa Monica, CA (US)

(73) Assignee: TRI-STAR TECHNOLOGIES, El Segundo, CA (US)

Reexamination Request:
No. 90/012,865, May 10, 2013

Reexamination Certificate for:
Patent No.: 6,429,889
Issued: Aug. 6, 2002
Appl. No.: 09/360,233
Filed: Jul. 23, 1999

(51) Int. Cl.
*B41J 2/175* (2006.01)
*B41M 5/26* (2006.01)
*A61K 9/20* (2006.01)
*B41J 2/44* (2006.01)

(52) U.S. Cl.
CPC .............. *B41M 5/26* (2013.01); *B41J 2/17566* (2013.01); *B41J 2/442* (2013.01); *A61K 9/2072* (2013.01); *B41J 2002/17573* (2013.01)

(58) Field of Classification Search
None
See application file for complete search history.

(56) References Cited

To view the complete listing of prior art documents cited during the proceeding for Reexamination Control Number 90/012,865, please refer to the USPTO's public Patent Application Information Retrieval (PAIR) system under the Display References tab.

*Primary Examiner* — Hetul Patel

(57) ABSTRACT

A unique method of marking individual consumable articles such as tablets, pills, and the like on the fly, without the deposition of ink or other marking materials on their surfaces, without degrading the articles, and without precise positioning and holding of the articles. Titanium dioxide is provided in a visible layer of the consumable articles in an amount that is effective to provide a mark when exposed to an effective amount of ultraviolet laser energy. The energy is emitted in a predefined pattern on the surface of the articles so as to define the desired marking pattern. Marking is effectively instantaneous, thereby permitting the target articles to be marked while in motion to efficiently and inexpensively provide marking rates that are as much as twenty times more than those provided by prior art ink deposition systems. Marking can be accomplished even when the articles are encapsulated in ultraviolet transparent packaging.

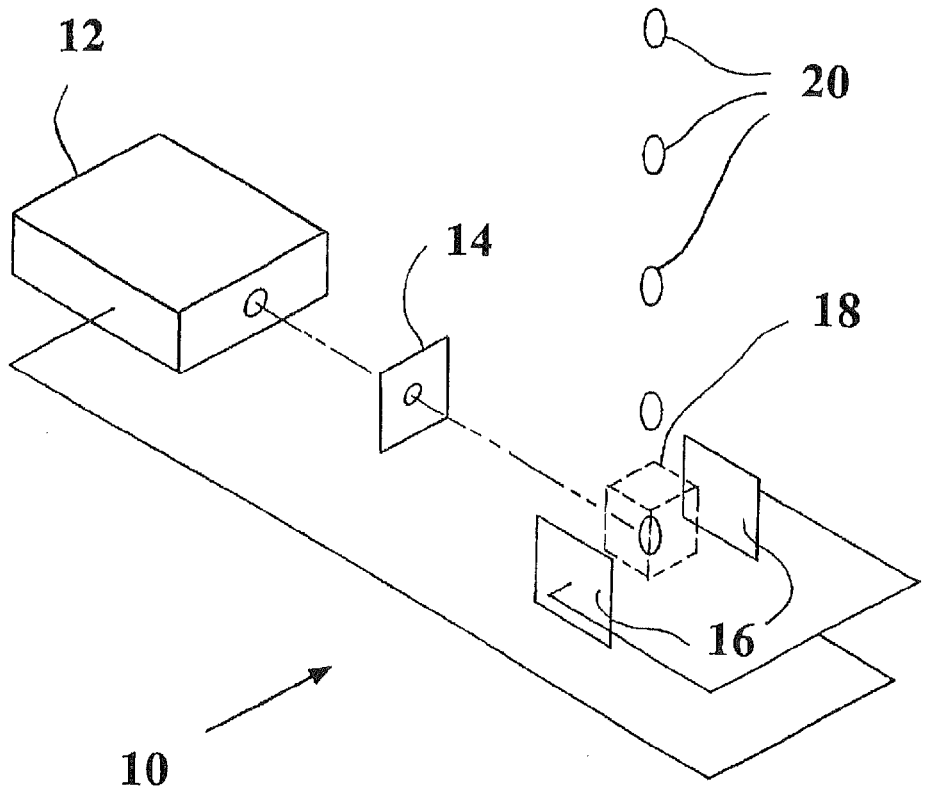

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

The patentability of claims 13, 18 and 19 is confirmed.

Claims 1-12 and 14-17 are cancelled.

\* \* \* \* \*